United States Patent
De Luca et al.

(10) Patent No.: US 11,168,037 B2
(45) Date of Patent: Nov. 9, 2021

(54) PROCESS FOR THE HALOGENATION AT THE ALPHA-H POSITION OF ALKYLARENES VARIOUSLY SUBSTITUTED ON THE AROMATIC RING

(71) Applicants: UNIVERSITA' DEGLI STUDI DI CAGLIARI, Cagliari (IT); UNIVERSITA' DEGLI STUDI DI SASSARI, Sassari (IT)

(72) Inventors: Lidia Vera Giovanna De Luca, Sassari (IT); Silvia Gaspa, Osilo (IT); Antonio Valentoni, Pattada (IT); Gabriele Mulas, Sassari (IT); Andrea Porcheddu, Ittiri (IT)

(73) Assignees: UNIVERSITÀ DEGLI STUDI DI SASSARI, Sassari (IT); UNIVERSITÀ DEGLI STUDI DI CAGLIARI, Cagliari (IT)

( * ) Notice: Subject to any disclaimer, the term of this patent is extended or adjusted under 35 U.S.C. 154(b) by 0 days.

(21) Appl. No.: 16/757,326

(22) PCT Filed: Oct. 17, 2018

(86) PCT No.: PCT/IB2018/058050
§ 371 (c)(1),
(2) Date: Apr. 17, 2020

(87) PCT Pub. No.: WO2019/077520
PCT Pub. Date: Apr. 25, 2019

(65) Prior Publication Data
US 2021/0188733 A1    Jun. 24, 2021

(30) Foreign Application Priority Data

Oct. 17, 2017    (IT) .................. 102017000116962

(51) Int. Cl.

| | | |
|---|---|---|
| *C07B 39/00* | (2006.01) | |
| *C07C 17/06* | (2006.01) | |
| *C07C 253/30* | (2006.01) | |
| *C07C 201/14* | (2006.01) | |
| *C07D 213/26* | (2006.01) | |
| *C07D 215/12* | (2006.01) | |
| *C07D 217/14* | (2006.01) | |
| *C07C 45/41* | (2006.01) | |

(52) U.S. Cl.
CPC .............. *C07B 39/00* (2013.01); *C07C 17/06* (2013.01); *C07C 45/41* (2013.01); *C07C 201/14* (2013.01); *C07C 253/30* (2013.01); *C07D 213/26* (2013.01); *C07D 215/12* (2013.01); *C07D 217/14* (2013.01)

(58) Field of Classification Search
CPC ......... C07B 39/00; C07C 17/06; C07C 45/41; C07C 201/14; C07C 253/30; C07D 213/26; C07D 215/12; C07D 517/14
USPC ........................................................ 546/253
See application file for complete search history.

(56) References Cited

PUBLICATIONS

International Search Report and Written Opinion for PCT/IB2018/058050, dated Dec. 17, 2018.
Combe, Sascha H., et al., "Mild Aliphatic and Benzylic Hydrocarbon C-H Bond Chlorination Using Trichloroisocyanuric Acid," J. Org. Chem., 82(5): 2407-2413 (2017).
Memoli, Kevin A., "Synthesis of a novel diazepine," J. Heterocyclic Chem., 44(4):927-928 (2007).
Mishra, Abhaya K., et al., "Trihaloisocyanuric Acids as Atom-Economic Reagents for Halogenation of Aromatics and Carbonyl Compounds in the Solid State by Ball Milling," Eur. J Org. Chem., 2015(12):2733-2738 (2015).
Xu, et al., "Development of a Scaleable Synthesis of NDT 9533750, a Key Intermediate to a Series of Novel Subtype Preferring GABA A Partial Agonists," Organic Process Research & Development, 11:716-720 (2007).
Zhou, et al., "Click reaction-mediated functionalization of near-infrared pyrrolopyrrole cyanine dyes for biological maging applications," RSC Adv., 3(19)6756-6758 (2013).
Pati, Subas C. and Sarangi, Chintamani, "Chlorination of Toluene & Substituted Toluenes by Trichloroisocyanuric Acid A Kinetic Investigation," Indian Journal of Chemistry, 24A:745-747 (1985).

*Primary Examiner* — Kristin A Vajda
(74) *Attorney, Agent, or Firm* — Troutman Pepper Hamilton Sanders LLP

(57) ABSTRACT

A process that allows halogenation at the alpha-H position of alkylarenes, optionally further substituted on the aromatic or heteroaromatic ring, is described.

11 Claims, No Drawings

PROCESS FOR THE HALOGENATION AT THE ALPHA-H POSITION OF ALKYLARENES VARIOUSLY SUBSTITUTED ON THE AROMATIC RING

This application is a national stage application under 35 U.S.C. § 371 of PCT Application No. PCT/IB2018/058050, filed Oct. 17, 2018, which claims the priority benefit of Italian Patent Application No. 102017000116962, filed Oct. 17, 2017.

FIELD OF THE INVENTION

The present invention relates to the field of processes for the synthesis of chemical products, in particular to a process for the halogenation at the alpha-H position of alkylarenes, optionally variously substituted on the aromatic ring.

STATE OF THE ART

As it is known, alkylarenes halogenated on the alkyl chain, such as for example benzyl chloride, are important intermediates in industrial preparations, for example for the preparation of drugs based on amphetamines, artificial resins, dyes, additives for fuels, and solutions for photographic development (Ullmann's Encyclopedia of Industrial Chemistry, Weinheim: Wiley-VCH, 2005, https://doi.org/10.1002%2F14356007.a06_233.pub2).

In particular, the industrial production of benzyl chloride is based on two main methods.

The first one (see Scheme 1 (a)) is the thermal or photochemical chlorination, in both batch and continuous reactors, of toluene with chlorine gas where a hydrogen atom is replaced by a chlorine atom. The chlorination of toluene proceeds through consecutive reactions wherein benzyl chloride is generated together with benzyl dichloride and benzyl trichloride by-products (classified as dangerous substances under TSCA), and o-, m- and p-chlorotoluene derived from the aromatic chlorination of the alkyl chloride products ring.

The second method (see Scheme 1 (b)), used industrially, is the chloromethylation of benzene (Gustave Louis Blanc Bull. Soc. Chim. France 1923, 33, 313, Whitmore, F C, Ginsburg, Abram, Rueggeberg, Walter, Tharp, I., Nottorf, H., Cannon, M., Carnahan, F., Cryder, D, FLeming, G., Goldberg, G., Haggard, H., Herr, C., Hoover, T., Lovell, H., Mraz, R., Noll, C., Oakwood, T., Patterson, H., Van Strien, R., Walter, R., Zook, H., Wagner, R., Weisgerber, C., Wilkins, J. (May 1946). "Chloride by Chloromethylation of Benzene, Laboratory and Pilot Plant Studies, 38 (5): 478-485), which is generally made by treating benzene with paraformaldehyde, hydrogen chloride gas, and anhydrous zinc chloride.

SCHEME 1 a)

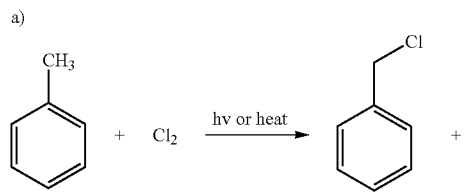

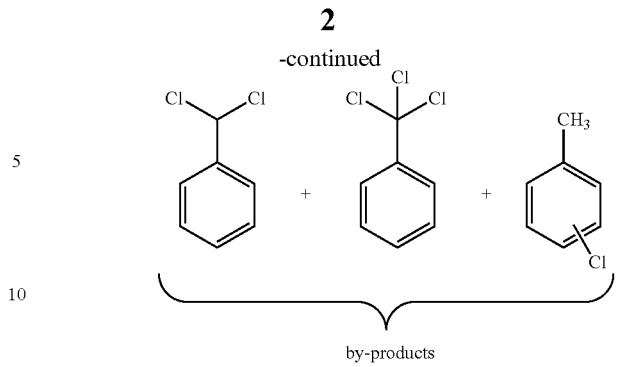

by-products b)

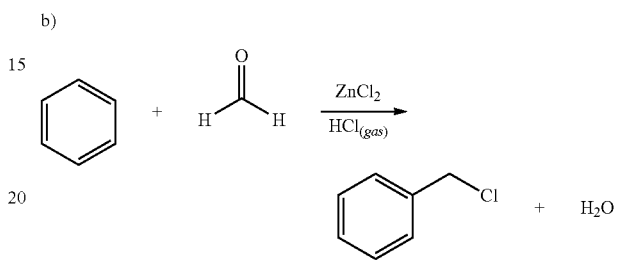

These methods suffer from huge limitations due to the use of corrosive gaseous reagents (HCl, $Cl_2$) that are difficult to handle, reactor complexity due to the use of gaseous components, harsh reaction conditions, also with very low yields and conversions in the desired product (around 40%).

Furthermore, several examples of chlorination of the methyl group have been reported in the literature, which envisage the use of chlorinating agents such as $Cl_2$, $SO_2Cl_2$, NaOCl, tBuOCl, $Et_4NCl$, but also in these cases reaction conditions, yields, and conversions are not satisfactory.

In particular, in S. H. Combe, A. Hosseini, A. Parra, P. R. Schereiner, J. Org. Chem. 2017, 82, 2407-2413 (see Scheme 2) the use of trichloroisocyanuric acid (TCCA), a commercially available and low-cost reagent, widely used for disinfecting pools, hotels and public places, and in industrial processes for preserving fruit and vegetables, as a chlorinating agent is described.

SCHEME 2

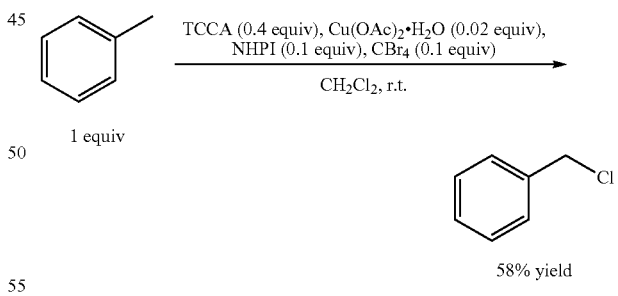

The method, however, does not have an optimal stoichiometric ratio of the reagents, and involves the use of a metal catalyst ($Cu(OAc)_2$), a radical initiator ($CBr_4$), an additive (NHPI, N-Hydroxyphthalimide), and methylene chloride as a solvent. The reaction provides the product with a yield of 58%, and an incomplete conversion.

Given the above, it is evident the interest, both scientific and industrial, to develop a green methodology, occurring with high yield and high conversions, to perform the chlorination of the methyl group of toluene and, in general, of alkylarenes optionally substituted on the aromatic ring.

SUMMARY OF THE INVENTION

A process that allows halogenation in the alpha-H position of alkylarenes, optionally further substituted on the aromatic or heteroaromatic ring, by reaction of the corresponding not halogenated alkylarenes exclusively with trichloroisocyanuric acid under irradiation with visible light, is described.

DETAILED DESCRIPTION OF THE INVENTION

The present process enables to overcome the aforementioned problems, by allowing to obtain alkylarenes selectively halogenated on the carbon atom of the alkyl substituent directly bonded to the aromatic or heteroaromatic ring by the exclusive use of the respective non-halogenated alkylarene and trichloroisocyanuric acid under irradiation with visible light.

In other words, the object of the present invention is a process for the production of alkylarenes selectively halogenated on the carbon atom of the alkyl substituent directly bonded to the aromatic or heteroaromatic ring, said process comprising contacting the respective non-halogenated alkylarene exclusively with acid trichloroisocyanuric acid under irradiation with visible light, in the total absence of solvents and any metal catalysts or chemical additives.

According to the invention, alkylarenes means compounds consisting of an aromatic or heteroaromatic ring having at least one alkyl chain as a substituent. The aromatic ring may be, for example: benzene, pyridine, quinoline, isoquinoline, pyrrole.

Alkyl means linear or branched alkyls having from 1 to 5 carbon atoms. As said, in addition to the above alkyl chain, the aromatic ring may be further substituted, for example by the following groups: $CH_3$, $C(CH_3)_3$, Cl, CN, $NO_2$, F, phenyl. Hereinbelow, the halogenation of toluene according to Scheme 3, reported below, is described in detail.

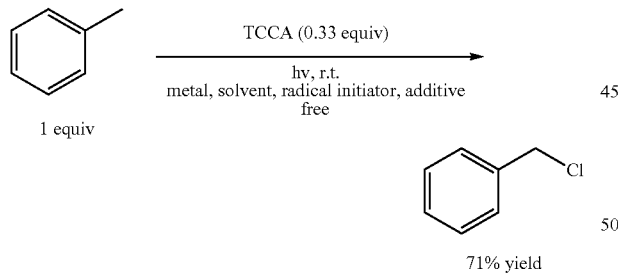

According to the invention, the starting products, toluene and trichloroisocyanuric acid, are in a stoichiometric ratio of between 4:2 and 2:0.5, preferably 3:1.

The process is carried out simply by mixing the reagents in a reactor and exposing the mixture to irradiation, at room temperature and under stirring; benzyl chloride is then collected by filtration.

The reaction times are generally of between 5 minutes and 12 hours, and the reaction is preferably carried out at room temperature, generally between 20 and 35° C., and under an inert atmosphere (for example, under argon).

Irradiation may be carried out either with a solar simulator or with a simple exposure to sun of the reaction reactor, which must obviously be made of a sunlight permeable material (for example, transparent colourless glass). Irradiation can also be achieved by using artificial light, such as a tungsten lamp or a blue led.

The reaction occurs in the total absence of solvents and any metal catalysts or chemical additives.

The reaction product is easily isolated by simple filtration on a silica pad, which allows to readily eliminate the isocyanuric acid formed as a result of the reaction, and the benzyl dichloride (the only by-product of the reaction, since no by-products deriving from the chlorination of the benzene ring are formed) which is formed in very small amounts (18%).

Furthermore, the conversion of toluene is almost quantitative (94%, also in this case the highest ever achieved so far). When the reaction was carried out using artificial light, such as a tungsten lamp or a blue led, benzyl chloride was obtained in yields of 70% and 71%, respectively.

Example 3.6 mmol (0.3318 g) of toluene are placed into a 25 mL two-necked flask, equipped with a magnetic stirrer, under an argon atmosphere; then, 1.2 mmol (0.279 g) of trichloroisocyanuric acid are added.

The flask is placed on a shaker and left under the solar simulator for 8 h at room temperature (25° C.).

The reaction is monitored by thin layer chromatography (TLC) and NMR analysis, and finally, when toluene concentration is lower than 6%, the product is purified through a silica pad.

The characterization of benzyl chloride obtained by nuclear magnetic resonance (NMR) spectroscopy is reported below:

Colourless oil; (0.346 g, 76% yield).

$^1$H NMR (400 MHz, $CDCl_3$) δ: 7.48-7.29 (m, 5H), 4.61 (s, 2H).

$^{13}$C NMR (100 MHz, $CDCl_3$) δ: 137.5, 128.7, 128.5, 128.4, 46.2.

The spectroscopic data obtained are in agreement with the data reported in the literature (S. H. Combe, A. Hosseini, A. Parra, P. R. Schreiner, *The Journal of Organic Chemistry* 2017, 82, 2407-2413).

Proceeding in an analogous way, starting from the respective alkylarene compounds, optionally further substituted on the aromatic (or heteroaromatic) ring, the products reported below were obtained with similar yields and purity:

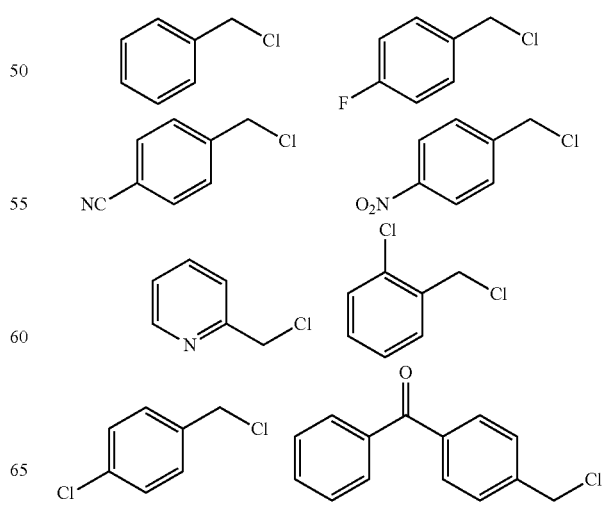

-continued

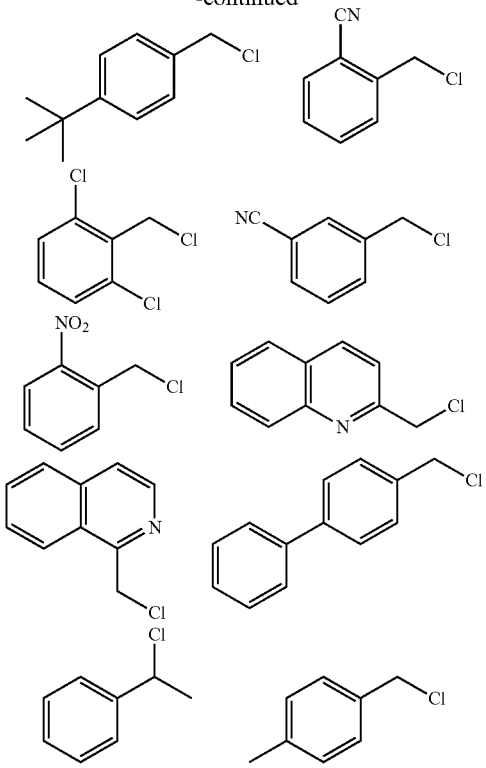

The present process is therefore configured as a green, solvent free process, with very high yields and conversions, and with a very simple product isolation procedure (filtration through a silica pad). Therefore, it allows to avoid the use of any solvents, the use of harsh reaction conditions, the atom economy of the process is very high, and yields and conversions are optimal.

The invention claimed is:

1. A process for the preparation of alkylarenes selectively halogenated on the carbon atom of the alkyl substituent directly bonded to the aromatic or heteroaromatic ring by reaction of the respective non-halogenated alkylarene compound exclusively with trichloroisocyanuric acid in the presence of irradiation with visible light, in the total absence of solvents and any metal catalysts or chemical additives.

2. The process according to claim 1, wherein alkylarenes are compounds consisting of an aromatic or heteroaromatic ring having at least one alkyl chain as a substituent.

3. The process according to claim 1, wherein said aromatic or heteroaromatic ring is selected from: benzene, pyridine, quinoline, and isoquinoline, and alkyl is a linear or branched alkyl having from 1 to 5 carbon atoms.

4. The process according to claim 1, wherein said aromatic or heteroaromatic ring is further substituted with one or more substituents selected from: $CH_3$, $C(CH_3)_3$, Cl, CN, $NO_2$, F, and phenyl.

5. The process according to claim 1, wherein the starting products of alkylarene/trichloroisocyanuric acid are in a stoichiometric ratio of between 4:2 and 2:0.5.

6. The process according to claim 1, wherein the starting products are reacted under solar light irradiation for a time of between 5 minutes and 12 hours at a temperature between 20 and 35° C., and under an inert atmosphere.

7. The process according to claim 6, wherein the irradiation is carried out with a solar simulator, or tungsten lamp, or blue led, or by simply exposing the reaction reactor to the sun.

8. The process according to claim 1, wherein the final product is isolated by filtration through a silica pad.

9. The process according to claim 1, wherein the alkylarene is toluene and the obtained product is benzyl chloride.

10. The process according to claim 1, wherein the following final product is obtained:

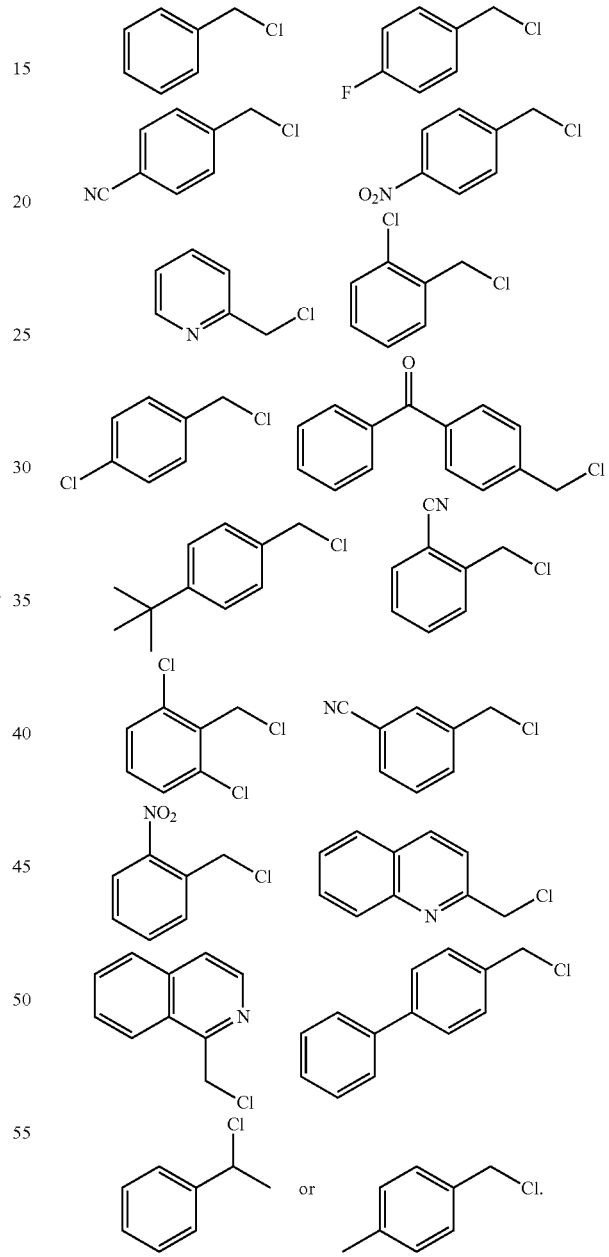

11. The process according to claim 5, wherein the starting products are in a stoichiometric ratio of 3:1.

* * * * *